(12) United States Patent
Shulman

(10) Patent No.: US 6,174,899 B1
(45) Date of Patent: Jan. 16, 2001

(54) ORALLY ADMINISTERED ANALGESIC COMPOSITION COMPRISING MYFADOL

(76) Inventor: Morton Shulman, 1115 Thorntree La., Highland Park, IL (US) 60035

( * ) Notice: Under 35 U.S.C. 154(b), the term of this patent shall be extended for 0 days.

(21) Appl. No.: 09/079,015

(22) Filed: May 14, 1998

(51) Int. Cl.[7] ........................ A01N 43/40; A61K 31/445
(52) U.S. Cl. ............................................. 514/317
(58) Field of Search ............................... 514/317

(56) References Cited

PUBLICATIONS

Shulman et al.: Studies With Myfadol, A New Analgesic Agent. Anesthesia And Analgesia . . . Current Researches, vol. 49, No. 6, Nov.–Dec., 1970, pp. 905–911.

Kugita et al.: 3–Alkyl–3–phenylpiperidine Derivatives As Analgesics. J. Med. Chem. 8:313–316 (May) 1965.

Remington's Pharmaceutical Sciences, 18th Edition, Mack Publishing Company, Easton, Pennsylvania, 1990, Chapter 91.

Kugita et al., "3–Alkyl–3–phenylpiperidine derivatives as analgesics. II", J. Med. Chem. 8:313–316, May 1965.*

* cited by examiner

*Primary Examiner*—Dwayne C. Jones
(74) *Attorney, Agent, or Firm*—Marshall, O'Toole, Gerstein, Murray & Borun

(57) ABSTRACT

An orally administered analgesic product comprises 250–1,000 mg of myfadol and a carrier for the myfadol. The orally administered product may be a solid or a liquid. The analgesic effect of the product lasts for 2 to 4 hours or more. The product contains more than 4 mg of myfadol per kg of body weight of the human patient to whom the product is administered. The solid product may contain a delayed release agent that extends the analgesic effect of the myfadol to a total time of up to 12 hours.

57 Claims, No Drawings

ORALLY ADMINISTERED ANALGESIC COMPOSITION COMPRISING MYFADOL

BACKGROUND OF THE INVENTION

The present invention relates generally to analgesic compositions and methods for administering these compositions and more particularly to analgesic compositions comprising myfadol and to methods for administering these compositions orally.

Analgesic compositions are pain relieving agents. Familiar analgesic compositions are aspirin and ibuprofin, both of which are non-steroidal antiinflammatory drugs (NSAID). A problem with NSAID-type analgesic compositions is that they have a plateau effect: they do a good job of relieving relatively mild levels of pain, but they are not good at relieving relatively severe levels of pain. Relief from severe levels of pain often requires the use of opioids.

Opioid analgesic compositions are narcotic compositions, and they have drawbacks. Tolerance and addiction can develop after repeated use. In addition, opioid analgesic compositions are capable of producing respiratory depression, excessive sedation, and, on occasion, cardiovascular depression.

It would be desireable to provide an analgesic composition which has the pain-relieving properties of opioid analgesic compositions but without the drawbacks which accompany their use. It would be most desireable to produce an analgesic composition having the properties described in the preceding sentence and which can be readily administered orally.

The analgesic composition, myfadol, has been administered by injection, both intravenously and intramuscularly. It has pain relieving properties comparable to those of opioid analgesic compositions, yet it produces less undesired side effects than opioid analgesic compositions. There is a report on tests conducted with myfadol administered by injection to humans; the report is in Shulman et al.: Studies With Myfadol, A New Analgesic Agent. Anesthesia And Analgesia . . . Current Researches, Vol. 49, No. 6, November–December 1970, p. 905; and the disclosure therein is incorporated herein by reference. The Shulman publication reports on the efficacy and side effects produced by various dosages of myfadol, expressed as milligrams of myfadol per kilogram of human patient body weight. From the standpoint of both efficacy and side effects, a dosage of 1.0 mg/kg was found to be superior to both 0.5 and 1.5 mg/kg. The Shulman publication concludes (at page 910) that single intravenous dosages of myfadol should not exceed 1 mg/kg.

When one desires to introduce orally an analgesic composition that has previously been introduced by injection, it is generally necessary to employ larger dosages of the analgesic composition. This is due to the so-called "first pass" effect produced by the liver which metabolizes an orally administered dosage of an analgesic composition and renders it ineffective up to a certain maximum amount. Anything over that amount is significantly effective. The "first pass" effect also eliminates side effects for all analgesic dosages up to the maximum amount of oral dosage which is ineffective.

Generally, one can tolerate an oral dosage that is 2–3 times greater than the maximum amount employed when administration is by injection, without producing undesireable side effects, while at the same time obtaining a significant pain-relieving effect. However, when myfadol was administered orally in those amounts (i.e. 2–3 mg/kg of human patient body weight), there was no significant pain relief.

SUMMARY OF THE INVENTION

In accordance with the present invention, it has been determined that, when myfadol is administered orally, the dosage must be greater than 4 mg. of myfadol per kilogram of body weight of the human patient. Preferably the dosage is 5–10 mg/kg. The resulting analgesic effect lasts for at least two hours for dosages at the lower end of the range (e.g. 4 or 5 mg/kg), and up to four hours or more (e.g. six hours) for dosages at the upper end of the range (e.g. 10 mg/kg).

The dosage may be administered as either a solid or a liquid. When the dosage is administered as a solid, it is part of a pill that may contain both myfadol and a carrier for the myfadol; the carrier may be in the form of a sustained release agent. When the dosage is administered as a liquid, the liquid contains both myfadol and a non-toxic, ingestible ingredient comprising a solvent or a suspending agent for the myfadol.

A typical pill comprises 250–1,000 mg. of myfadol, preferably 300–500 mg. A dosage administered as a liquid would contain similar amounts of myfadol.

Other features and advantages are inherent in the subject matter claimed and disclosed or will become apparent to those skilled in the art from the following detailed description.

DETAILED DESCRIPTION

Myfadol is described in the aforementioned Shulman publication, and myfadol is also described in Kugita et al.: 3-Alkyl-3-phenylpiperidine Derivatives As Anagesics. J. Med. Chem. 8:313–316 (May) 1965 (see formula No. 11 in Table II); and the disclosure therein is incorporated herein by reference. Myfadol has the following structural formula:

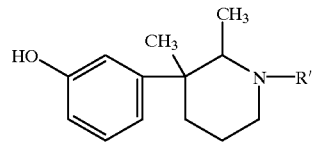

where R' is $C_6H_5COCH_2$. R' has the following structural formula:

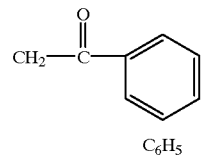

An advantage of myfadol is that, unlike opioids, myfadol is not a narcotic, i.e. myfadol is not addictive in the sense that myfadol will not prevent morphine withdrawal in monkeys. This property of myfadol is reported in the Shulman publication noted above.

Myfadol is believed to be a composition of the type known as "agonist antagonist". An agonist is a material which works at a receptor site in the body of the human patient. A receptor site is an area on a cell to which the agonist physically binds and where the agonist then exerts its effect on that cell. An antagonist is a material which replaces the agonist at the receptor site and prevents the agonist from working there. It is believed that, in an agonist antagonist, the antagonist property of the composition limits over-activity by the agonist and prevents it from having toxic effects at the receptor site.

In the aforementioned Shulman publication, there is a quantitative discussion of the analgesic effect of myfadol, and the side effects produced by myfadol, when administered by injection, both intravenously and intramuscularly. The Shulman publication indicates that there is both a good analgesic effect and an absence of side effects when one employs an injection dosage of 1 mg/kg. It is believed that the same analgesic effect and the same absence of side effects will be produced by an orally administered dosage in accordance with the present invention.

The following discussion is based upon the premise that a typical human adult has a body weight of about 70 kg (154 lbs.) and that a minimum body weight for a human adult is about 50 kg (110 lbs.).

Myfadol may be administered orally to a human adult patient either as a solid or as a liquid. In either case, there should be a dosage of greater than about 4 mg/kg of body weight of the human adult patient, preferably 5–10 mg/kg. For a typical human adult patient this works out to be a dosage of 280 mg or more, preferably 350–700 mg. In its broadest sense, the present invention comprises a dosage in the range 250–1,000 mg of myfadol, e.g. 300–500 mg of myfadol.

The bigger the dosage of myfadol, the longer lasting is the pain relief. A dosage of 250 mg of myfadol should produce pain relief lasting about two hours; a dosage of 1,000 mg of myfadol should produce pain relief for a time in the range 4–6 hours.

When myfadol is administered orally as a solid, the myfadol may be contained in a pill which, as that term is used herein, includes both a capsule and a tablet. When the myfadol is contained in a pill, the pill may also contain a carrier for the myfadol. The carrier can be any composition heretofore used as a carrier for dosages of medicaments introduced orally, so long as the carrier does not adversely affect the properties imparted to the pill by the myfadol. The carrier may be in the form of a sustained release agent of which more will be discussed subsequently.

When myfadol is administered orally as a liquid, it is part of a liquid product also comprising either a solvent for the myfadol or a suspending agent for the myfadol. In either case, the solvent or suspending agent is non-toxic and ingestible. Both the solvent and the suspending agent are a minor part of a liquid carrier comprising water as a major part. One example of a suspending agent is polyethylene glycol. Other appropriate glycols may also be used as suspending agents.

One type of product in accordance with the present invention is provided as a solid dosage comprising myfadol, as the analgesic agent, and a delayed release agent, with the myfadol being present in two parts. The delayed release agent (sometimes referred to as a sustained release agent) cooperates with one of the two parts of myfadol but not with the other part of the myfadol. As a result, in response to the oral administration of the solid dosage to a human patient, there is initially released in the patient's gastrointestinal tract, substantially unrestrained by the delayed release agent, sufficient myfadol to produce a noticeable analgesic effect relatively quickly; this is the myfadol part that does not cooperate with the delayed release agent. Subsequently, there is released sufficient additional myfadol to maintain the analgesic effect for a time substantially beyond the time attributable to the initial release of myfadol; the subsequently released myfadol is the myfadol part that does cooperate with the delayed release agent.

The product described in the preceding paragraph comprises a total myfadol content of 500–2,000 mg. The amount of myfadol available for the initial release is 250–1,000 mg., preferably 300–500 mg. The amount of myfadol available for the subsequent release is 50–100% of the weight of the initial release of myfadol.

The delayed release agent can be of the type which releases substantially all of the additional myfadol at substantially the same time, or it can be of the type which releases the additional myfadol incrementally over an extended period of time, preferably in substantially equal increments over the extended period of time. The extended period of time for the subsequent incremental release may be in the range 2–12 hours after the initial release. The initial release of myfadol produces an analgesic effect which lasts for at least two hours and up to four hours or more.

In one embodiment of the product described in the three preceding paragraphs, the initially releasable myfadol (the one part) is physically separate and discrete in the product from the subsequently releasable myfadol (the other part), but both parts of myfadol are contained in the same pill. In another embodiment of that product, the initially releasable myfadol is contained in one pill, and the subsequently releasable myfadol is contained in another pill. In this latter embodiment, the two pills are part of one package also comprising an enclosure containing the two pills.

Preferably both the initially releasable myfadol and the subsequently releasable myfadol are both contained in the same pill, but this type of arrangement is constrained by the total solid content of the product. The total solid content, comprising the initially releasable myfadol, the subsequently releasable myfadol and the delayed release agent, may constitute a mass whose volume is too large to contain in one orally administered pill. In such a case, one may employ the embodiment comprising two pills contained in a single package, with one pill containing the initially releasable myfadol and the other pill containing the subsequently releasable myfadol.

Examples of sustained or delayed release agents, the properties thereof, and the considerations involved in the employment thereof are described in Remington's Pharmaceutical Sciences, 18th Edition, Mack Publishing Company, Easton, Pennsylvania, 1990, in chapter 91 entitled "Sustained-Released Drug Delivery Systems", beginning at page 1676, particularly the section entitled "Oral Dosage Forms", beginning at page 1682. The disclosure in the publication described in the preceding sentence is incorporated herein by reference.

In one embodiment of a pill employing a delayed release agent, the pill may be composed of two separate, discrete layers, one atop the other: one such layer contains the initially releasable myfadol; the other such layer contains the subsequently releasable myfadol together with the delayed release agent. In this embodiment, the myfadol in the lower layer may be dispersed in a slowly soluble polymer carrier (the delayed release agent) and released incrementally over an extended period of time, e.g., two to twelve hours after the initial release.

Another form of a product employing a delayed release agent comprises a pill composed of an inner core and an outer layer; the outer layer comprises the initially releasable myfadol; and the inner core comprises the subsequently releasable myfadol. The delayed release agent comprises a soluble coating surrounding the inner core and separating the inner core from the outer layer. The thickness of the soluble coating determines the length of the delay. Once the coating has dissolved, substantially all of the myfadol in the inner core is released at substantially the same time. Depending upon the thickness of the soluble coating, all of the myfadol in the inner core can be released two hours after the initial release of myfadol or it can all be released up to six hours after the initial release, for example.

As an alternative, the inner core may itself be composed of a series of layers of myfadol with each layer of myfadol in the inner core separated from adjacent layers by a soluble coating. When a given soluble coating becomes exposed, it dissolves and releases the layer of myfadol previously surrounded by that coating, in turn exposing another soluble coating surrounding the next layer to be released. The net result is the release of several individual increments of myfadol at spaced intervals over an extended period of time, e.g., in the range 2–12 hours after the initial release of myfadol. The amount of myfadol in each increment or layer can be the same, or the amount can vary from layer to layer.

The foregoing detailed description has been given for clearness of understanding only and no unnecessary limitations should be understood therefrom, as modifications will be obvious to those skilled in the art.

What is claimed is:

1. A solid product for inducing and maintaining analgesia in a human patient by oral administration, said product comprising:
   250–2,000 mg of myfadol as the analgesic agent.
2. A product as recited in claim 1 wherein:
   said solid product is in the form of a pill comprising 250–1,000 mg of myfadol.
3. A product as recited in claim 2 wherein:
   said pill comprises 300–500 mg of myfadol.
4. A product as recited in claim 2 wherein:
   said product produces an analgesic effect which lasts for at least two hours.
5. A product as recited in claim 4 wherein:
   said analgesic effect lasts up to four hours or more.
6. A product as recited in claim 2 wherein:
   said pill contains more than 4 mg of myfadol per kilogram of body weight of said human patient.
7. A product as recited in claim 6 wherein:
   said pill contains 5–10 mg of myfadol per kilogram of body weight of said human patient.
8. A solid product as recited in claim 1 and further comprising:
   a delayed release agent; and
   means, responsive to the oral administration of said solid product to a human patient, for initially releasing, in the patient's gastrointestinal tract, substantially unrestrained by said delayed release agent, sufficient myfadol to produce a noticeable analgesic effect relatively quickly;
   said delayed release agent comprising means for enabling the subsequent release of sufficient additional myfadol to maintain said analgesic effect for a time substantially beyond the time attributable to the initial release of myfadol.
9. A product as recited in claim 8 and comprising a total myfadol content of 500 to 2,000 mg.
10. A product as recited in claim 9 wherein:
    the amount of myfadol available for said initial release is 250 to 1,000 mg.
11. A product as recited in claim 10 wherein:
    the amount of myfadol available for said initial release is 300–500 mg.
12. A product as recited in claim 10 wherein:
    the amount of myfadol available for said subsequent release is 50 to 100% of the weight of said initial release of myfadol.
13. A product as recited in any of claims 8–12 wherein:
    said means for subsequently releasing additional myfadol comprises means for releasing substantially all of said additional myfadol at substantially the same time.
14. A product as recited in any of claims 8—12 wherein:
    said means for subsequently releasing additional myfadol comprises means for subsequently releasing said additional myfadol incrementally over an extended period of time.
15. A product as recited in claim 14 wherein:
    the myfadol released during said subsequent incremental release is released in substantially equal increments over an extended period of time.
16. A product as recited in claim 14 wherein:
    said subsequent incremental release occurs over an extended period of time in the range 2 to 12 hours after said initial release.
17. A product as recited in claim 16 wherein:
    said initial release of myfadol produces an analgesic effect which lasts for at least two hours.
18. A product as recited in claim 17 wherein:
    said analgesic effect produced by said initial release lasts up to four hours or more.
19. A product as recited in claim 8 wherein:
    (a) said initially releasable myfadol is physically separate and discrete in said product from (b) said subsequently releasable myfadol.
20. A product as recited in claim 19 wherein:
    said initially releasable myfadol is contained in one pill and said subsequently releasable myfadol is contained in another pill.
21. A package comprising the two pills recited in claim 20, and an enclosure containing said two pills.
22. A product as recited in claim 8 wherein:
    said initially releasable myfadol and said subsequently releasable myfadol are both contained in the same pill.
23. A method for inducing and maintaining analgesia in a human patient by oral administration, said method comprising:
    providing a product comprising, as the analgesic agent, 250–2,000 mg of myfadol;
    and administering said product orally to said human patient.
24. A method as recited in claim 23 wherein:
    said product is provided as a solid product in the form of a pill comprising 250–1,000 mg of myfadol.
25. A method as recited in claim 24 wherein:
    the amount of myfadol administered with said pill is greater than 4 mg of myfadol per kilogram of body weight of said human patient.
26. A method as recited in claim 25 wherein:
    the amount of myfadol administered with said pill is 5–10 mg of myfadol per kilogram of body weight of the human patient.
27. A method as recited in claim 24 wherein:
    said pill comprises 300–500 mg of myfadol.
28. A method as recited in claim 24 wherein:
    said pill produces, in response to said oral administration, an analgesic effect which lasts for at least two hours.
29. A method as recited in claim 28 wherein:
    said analgesic effect lasts up to four hours or more.
30. A method as recited in claim 23 and comprising:
    providing said product as a solid product comprising (i) said myfadol as the analgesic agent and (ii) a delayed release agent;

said solid product comprising means, responsive to the oral administration of said solid product to a human patient, for initially releasing in the patient's gastrointestinal tract, substantially unrestrained by said delayed release agent, sufficient myfadol to produce a noticeable analgesic effect relatively quickly;

said delayed release agent comprising means for enabling the subsequent release of sufficient additional myfadol to maintain said analgesic effect for a time substantially beyond the time attributable to the initial release of myfadol;

said solid product producing, in response to said oral administration, (a) an initial release in the patient's gastrointestinal tract, substantially unrestrained by said delayed release agent, of sufficient myfadol to produce a noticeable analgesic effect relatively quickly and then (b) a subsequent release of sufficient additional myfadol to maintain said analgesic effect for a time substantially beyond the time attributable to the initial release of myfadol.

31. A method as recited in claim 30 wherein:
said initial release of myfadol comprises more than 4 mg of myfadol per kilogram of body weight of said human patient.

32. A method as recited in claim 30 wherein:
said initial release of myfadol comprises 5–10 mg of myfadol per kilogram of body weight of the patient.

33. A method as recited in claim 30 herein:
the total amount of myfadol released during said initial release and said subsequent release is in the range 500–2,000 mg.

34. A method as recited in claim 33 wherein:
said initial release comprises 250–1,000 mg of myfadol.

35. A method as recited in claim 34 wherein:
said initial release comprises 300–500 mg of myfadol.

36. A method as recited in claim 34 wherein:
said subsequent release of myfadol comprises 50–100% of the weight of said initial release.

37. A method as recited in any of claims 30–36 wherein:
said subsequent release comprises releasing substantially all of said additional myfadol at substantially the same time.

38. A method as recited in claim 37 wherein:
said subsequent release occurs at least two hours after said initial release.

39. A method as recited in claim 38 wherein:
said subsequent release occurs up to four hours or more after said initial release.

40. A method as recited in any of claims 30–36 wherein:
said subsequent release comprises releasing said additional myfadol incrementally over an extended period of time.

41. A method as recited in claim 40 wherein:
said subsequent incremental release occurs in substantially equal increments over an extended period of time.

42. A method as recited in claim 40 wherein:
said subsequent incremental release occurs over an extended period of time in the range 2 to 12 hours after said initial release.

43. A method as recited in claim 42 wherein:
said initial release of myfadol produces an analgesic effect which lasts for at least two hours.

44. A method as recited in claim 43 wherein:
said analgesic effect produced by said initial release lasts up to four hours or more.

45. A method as recited in claim 30 and comprising:
maintaining (a) said initially releasable myfadol separate and discrete from (b) said subsequently releasable myfadol.

46. A method as recited in claim 45 and comprising:
containing said initially releasable myfadol in one pill and said subsequently releasable myfadol in another pill.

47. A method as recited in claim 46 and comprising:
enclosing the two pills recited in claim 44 in the same package, before said oral administration.

48. A method as recited in claim 45 and comprising:
containing said initially releasable myfadol and said subsequently releasable myfadol in the same pill.

49. A method as recited in claim 30 wherein:
the amount of myfadol provided for said initial release is greater than 4 mg of myfadol per kilogram of body weight of said human patient.

50. A method as recited in claim 49 wherein:
the amount of myfadol provided for said initial release is 5–10 mg of myfadol per kilogram of body weight of the human patient.

51. A method as recited in claim 49 wherein:
the amount of myfadol provided for said subsequent release is 50–100% of the weight of myfadol provided for said initial release.

52. A method as recited in claim 23 and comprising:
providing said product as a liquid product comprising (a) 250–1,000 mg of said myfadol, and (b) a non-toxic, ingestible solvent or suspending agent for said myfadol.

53. A method as recited in claim 52 wherein:
the amount of myfadol administered in said liquid product is greater than 4 mg of myfadol per kilogram of body weight of said human patient.

54. A method as recited in claim 53 wherein:
the amount of myfadol administered in said liquid product is 5–10 mg of myfadol per kilogram of body weight of said human patient.

55. A method as recited in claim 53 wherein:
said liquid product comprises 300–500 mg of myfadol.

56. A method as recited in claim 52 wherein:
said liquid product produces, in response to said oral administration thereof, an analgesic effect which lasts for at least two hours.

57. A method as recited in claim 56 wherein:
said analgesic effect lasts up to four hours or more.

\* \* \* \* \*